Dec. 23, 1975 D. J. S. BAILEY Plant Pat. 3,820
ROSE PLANT
Filed May 10, 1973
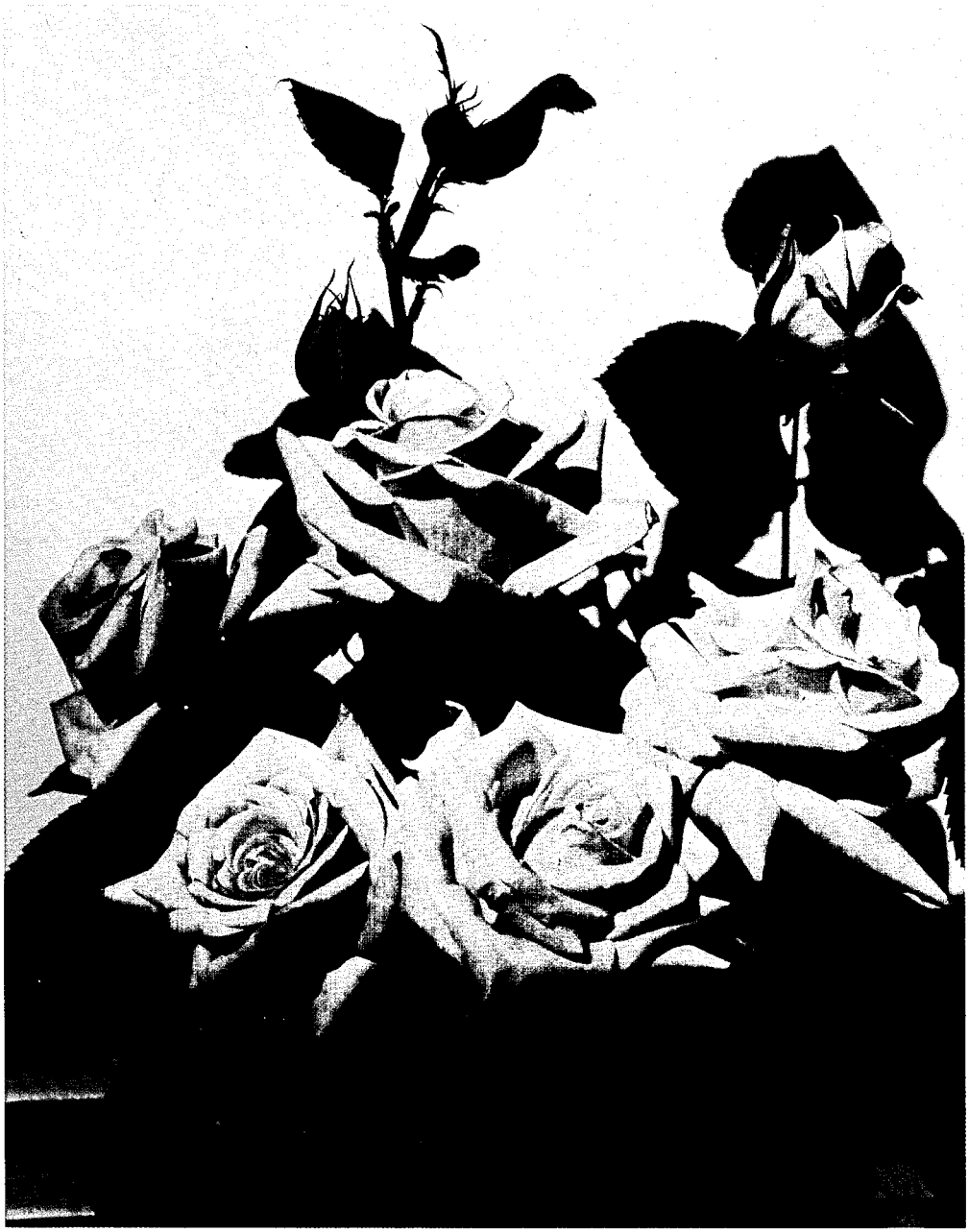

United States Patent

Plant Pat. 3,820

Patented Dec. 23, 1975

3,820

ROSE PLANT

Dorothy Jean Searles Bailey, Bakersfield, Calif., assignor to San Joaquin Rose Co., McFarland, Calif.

Filed May 10, 1973, Ser. No. 359,097

Int. Cl. A01h 5/00

U.S. Cl. Plt.—20 1 Claim

The present invention relates to a new and distinct variety of rose plant of the hybrid tea class, which was originated by me by crossing the rose variety known as "Queen Elizabeth" (Plant Pat. No. 1,259) with the variety known as "San Francisco" (Plant Pat. 2,045).

As the result of this breeding, I have produced a new and improved rose variety which is distinguished from its parents, as well as from all other rose varieties of which I am aware, as evidenced by the following unique combination of characteristics which are outstanding therein:

(1) A moderately tall, well-shaped plant having upright and well-branched canes;
(2) Abundant, medium large, heavy, dark green foliage;
(3) Continuous abundant bloom production from early spring until dormancy, with flowers single to long stems or two or several to a stem, on strong, medium long stems;
(4) Urn-shaped buds of approximately one inch length, of a bright red color, Orient Red $8^{19}$, with two or three foliaceous sepals;
(5) A high-centered bloom when half-opened, of a bright orange red color, general effect Signal Red $7^{19/1}$;
(6) The bloom consisting of from 40 to 50 petals, arranged regularly; and
(7) A light spicy fragrance.

In comparison with its parent varieties, the new variety has inherited a modified habit from the parent "Queen Elizabeth," having its good vigor and upright bush, but is not as tall a bush. The striking bright orange red color range is largely inherited from the parent "San Francisco," which is an intensely bright red variety but rather a weak grower. The great profusion of bloom resembles the bloom output of the parent "Queen Elizabeth"; the bloom form and size is intermediate between each parent, being larger than the bloom of "Queen Elizabeth," and a bit smaller than the bloom of "San Francisco."

The new variety most nearly resembles the established variety known as "Comanche." However, the distinction is clear-cut as the following comparison shows:

| | This Variety | "Comanche" |
|---|---|---|
| Bud: | | |
| Form | Urn shaped | Pointed or blunt. |
| Size | Approximately 1" | Approximately 1". |
| Color | Orient Red $8^{19}$ | Blood Red $8^{20}$. |
| Sepals | 5 | 7. |
| | 2 or 3 foliaceous | Every other foliaceous. |
| | Grey green tips | Top dark green. |
| Open bloom: | | |
| Form | High-centered | High-centered. |
| | Maintaining urn shape | Opening loose. |
| Color: | | |
| General effect | Signal Red $7^{19/1}$ | Claret Rose $0^{21}$. |
| Petal top | Scarlet 19 | Delft Rose $0^{20/1}$. |
| Petal bottom | Orient Red $8^{19/3}$ | Rose Opal $0^{22/1}$. |
| Number of petals. | 45 plus petaloids | 30 plus petaloids. |
| Finishing bloom: | | |
| Diameter | 3½" | 3½". |
| Form | Wide open | Wide open. |
| | Pistils and stamens exposed. | Pistils and stamens exposed. |
| Color | Petal tips Geranium Lake 20 shading to $^{20/1}$. | Delft Rose $0^{20}$. |

| | This Variety | "Comanche" |
|---|---|---|
| Reproductive parts: | | |
| Pistils | Bunched together and few. | Many, separate. |
| | Style light yellow | Top of style, red. |
| Anthers | Filaments short, rosy | Filaments longer, rosy. |
| | Anthers rounded, short | Anthers longer, narrow. |
| Ovule | Set well in V shaped receptacle. | Set on top of receptacle. |
| Blooming habit | Branching for blooms well down in plant. | Bloom in short clusters of 3-5. |
| Stems | Strong, long | Lighter, shorter. |
| | 12-18" long | 4-6" long. |
| Foliage | Dark green, semi-glossy | Dark green, semi-glossy. |
| | Leathery | Softer. |
| | Veins markedly yellow green. | Veins reddish. |
| | Leaf undersides grey-green. | Undersides reddish-greygreen. Edges reddish green. |
| Wood | Medium green | Reddish green. |
| Thorns | Moderately present | Moderately present. |
| | Base narrow, elliptical | Base narrow, elliptical. |
| | Yellowish green | Red green. |
| | ¼" base to tip | ⅜" base to tip. |

The cross that resulted in this new variety was made in 1962 by me, at Shafter, Calif. It was first asexually reproduced in 1964, also at Shafter, Calif., by means of budding. The distinguishing characteristics are held through succeeding propagations.

The accompanying photographs show typical specimens of the vegetative growth and flowers of my new variety in different stages of development and are depicted in color as nearly true as it is reasonably possible with color photography.

The following is a detailed description of my new variety, with color terminology in accordance with the Horticultural Colour Chart of the British Colour Council, except where general color terms of ordinary dictionary significance are obvious, as based upon observations of specimens grown at Shafter, Calif.:

TYPE: Half-hardy medium sized, upright bush habit; outdoor garden growing; seedling; for cut flowers and for garden decoration.

CLASS: Hybrid tea.

BREEDING: Seedling.

Seed parent—"Queen Elizabeth."

Pollen parent—"San Francisco."

DATE OF SOWING—1962.

PROPAGATION: Holds its distinguishing characteristics through succeeding propagations by budding.

FLOWER

CONTINUITY: Continuous.

FRAGNANCE: Light, spicy.

FLOWERS BORNE: Singly to a strong long stem or two to several to strong, medium long stems, in irregular clusters.

QUANTITY OF BLOOM: Abundant outdoors.

BUDS:

Peduncle—Medium in length; medium heavy; erect stiff; reddish-bronze; slightly rough; numerous red hairs and prickles.

Before calyx breaks: Size—Medium. Form—Pointed, oval, without a conspicuous neck; with foliaceous appendages on the surface of the bud; with slender, entire, much cut, foliaceous parts extending beyond the tip of the bud equal to ¾ or more of its length. Color—Chrysanthemum crimson $8^{24}$ (Plate 169) and Pod Green o61 (Plate 120).

As calyx breaks: Color—No significant change.

As first petal opens: Size—Medium. Form—Globular. Color— Outside—Orient Red $8^{19}$ (Plate 165);

inside—Scarlet 19 (Plate 19). Opening—It does open up well. It is not retarded or prevented from opening by cold, hot, wet, or dry weather.

BLOOM:

Size—When fully open—medium, 3 to 4½ inches.

Petalage—Very double; 40 to 50 petals arranged regularly.

Form—High centered at first; becoming open; petals being at first rolled outward; becoming later loosely rolled outward.

PETALS:

Texture—Thick; with inside velvety; with outside shiny.

Shape—Outside—round. Intermediate—ovate; sometimes scalloped with 1 notch. Inside—ovate.

This description of a newly opened flower was made from a rose grown outdoors, August 1971, Shafter, Calif.

Color—Outside petal: Outside surface—Orient red $8^{19}$ (Plate 165). Inside surface—Scarlet 19 (Plate 19). Intermediate petal: Outside surface—Orient red $8^{19}$. Inside surface—Scarlet 19. Inner petal: Outside surface—Orient red $8^{19/1}$. Inside surface—Scarlet 19.

This description was made from a rose that was open for three days, outdoors, August 1971, Shafter, Calif.

Color—Outside petal: Outside surface—Orient red $8^{19/3}$. Inside surface—Scarlet 19/1. Inside petal: Outside surface—Scarlet 19/2. Inside surface—Vermillion 18/1 (Plate 18).

General color effect—Newly opened flower—Signal Red $7^{19/1}$ (Plate 93). Three days open—Scarlet 19/1.

Behavior—Drop off cleanly; fading Geranium Lake 20 (Plate 20).

Flower longevity—Bush in garden, 5 days in August; cut roses grown outdoors, kept at living room temperatures, 5 days in October.

REPRODUCTIVE ORGANS

STAMENS: Medium in number; arranged irregularly about pistils; mixed with petaloids.

Color—Light Yellow.

FILAMENTS: Short; Rosy; many; most with anthers.

ANTHERS: Short; rounded; yellow; open at various times.

POLLEN: Moderate; yellow.

PISTILS: Few.

STYLES: Uneven; short and medium long; bunched; Light Yellow.

STIGMA: Light yellow.

OVARIES: All enclosed in the calyx.

HIPS: None observed.

SEPALS: Permanent; moderately long; straight; spear-shaped.

PLANT

FOLIAGE: Leaves compound of 5; abundant; medium large; heavy.

Leaflets—Ovoid; mucronate apex; margin doubly serrate.

Color — Mature — Upper surface—Dark Green; Under surface—Light Bronze-Red. Young—Upper surface—Green-Bronze; under surface—red.

Rachis (the supporting stem of the compound leaf)—Medium in thickness. Upper side—Slightly hairy.

Under side—Moderately supplied with glandular hairs.

Stipules—Medium in length; moderately narrow; moderately long points; turning out at an angle of less than 45°.

Disease and insect resistance—Unusually resistant to mildew and rust; tested by growing other varieties and comparing in Vista, Calif. and Shafter, Calif.

GROWTH:

Habit—Upright; bush; well-branched.

Growth—Vigorous.

Canes—Medium heavy.

Main stems—Bright green. Thorns—Few; medium long; straight; with long narrow base. Prickles—None. Hairs—None.

Branches—Bright green. Thorns—Several; medium long; straight; with long narrow base. Prickles—Several; Light Yellow. Hairs—None.

New shoots—Bright Bronze Red. Thorns—Several; medium long; straight; with long narrow base. Prickles—Several; reddish. Hairs—None.

I claim:

1. A new and distinct variety of rose plant of the hybrid tea class, substantially as herein shown and described, characterized particularly as to novelty by the unique combination of a moderately tall, well-shaped vigorous plant having upright and well-branched canes; abundant, medium large, heavy dark green foliage that has markedly superior resistance to mildew and rust; continuous abundant bloom production from early spring until fall dormancy, with flowers borne single on long stems or two or several on a branch, each on strong, medium long stem; urn-shaped buds of approximately one inch length, of a bright red color, Orient Red $8^{19}$, with two or three foliaceous sepals; a high-centered bloom when half-opened, of a bright orange red color, general effect Signal Red $7^{19/1}$; a graceful mature coloration of Geranium Lake 20, shading to Geranium Lake 20/1; a medium sized bloom consisting of from 40 to 50 petals arranged regularly; and a light spicy fragrance.

No references cited.

ROBERT E. BAGWILL, Primary Examiner